United States Patent [19]
DiMarzio et al.

[11] Patent Number: 5,883,717
[45] Date of Patent: *Mar. 16, 1999

[54] OPTICAL QUADRATURE INTERFEROMETRY UTILIZING POLARIZATION TO OBTAIN IN-PHASE AND QUADRATURE INFORMATION

[75] Inventors: Charles A. DiMarzio, Cambridge; Anthony J. Devaney, Boston; Scott C. Lindberg, Brighton, all of Mass.

[73] Assignee: Northeastern University, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 658,087

[22] Filed: Jun. 4, 1996

[51] Int. Cl.$^6$ .................................................... G01B 9/02
[52] U.S. Cl. ................................... 356/351; 356/359
[58] Field of Search .................................. 356/351, 359, 356/360

[56] References Cited

U.S. PATENT DOCUMENTS

| | | | |
|---|---|---|---|
| 3,620,589 | 11/1971 | Dudderar et al. | 356/351 |
| 4,183,671 | 1/1980 | Jacobson | 356/354 |
| 4,418,981 | 12/1983 | Stowe | 350/96.15 |
| 4,426,620 | 1/1984 | Buchenauer | 324/83 D |
| 4,514,054 | 4/1985 | Stowe | 350/96.15 |
| 4,789,240 | 12/1988 | Bush | 356/345 |
| 4,798,468 | 1/1989 | Ohuchi | 356/351 |
| 4,899,042 | 2/1990 | Falk et al. | 250/227 |
| 5,101,450 | 3/1992 | Olshansky | 385/3 |
| 5,200,795 | 4/1993 | Kim et al. | 356/345 |
| 5,289,256 | 2/1994 | Gramling | 356/345 |
| 5,367,175 | 11/1994 | Bobb | 250/577 |
| 5,491,552 | 2/1996 | Knuttel | 356/351 |
| 5,619,325 | 4/1997 | Yoshida | 356/351 |

Primary Examiner—Robert Kim
Attorney, Agent, or Firm—Weingarten, Schurgin, Gagnebin & Hayes LLP

[57] ABSTRACT

An optical quadrature interferometer is presented. The optical quadrature interferometer uses a different state of polarization in each of two arms of the interferometer. A light beam is split into two beams by a beamsplitter, each beam directed to a respective arm of the interferometer. In one arm, the measurement arm, the light beam is directed through a linear polarizer and a quarter wave plate to produce circularly polarized light, and then to a target being measured. In the other arm, the to reference arm, the light beam is not subject to any change in polarization. After the light beams have traversed their respective arms, the light beams are combined by a recombining beamsplitter. As such, upon the beams of each arm being recombined, a polarizing element is used to separate the combined light beam into two separate fields which are in quadrature with each other. An image processing algorithm can then obtain the in-phase and quadrature components of the signal in order to construct an image of the target based on the magnitude and phase of the recombined light beam.

27 Claims, 7 Drawing Sheets

OPTICAL QUADRATURE INTERFEROMETRY UTILIZING POLARIZATION TO OBTAIN IN-PHASE AND QUADRATURE INFORMATION

FIELD OF THE INVENTION

The present invention relates generally to interferometers and more particularly to quadrature interferometers.

BACKGROUND OF THE INVENTION

Mach-Zender interferometers and Michelson interferometers are known in the art. The interferometers typically include a beamsplitter which divides a signal from a light source into two separate signals which are in-phase with one another. One signal is sent through a reference arm which may include a compensation element. The other signal is sent through a measurement arm, in which the optical signal is exposed to some change in amplitude and phase. In the Mach-Zender interferometer, after the signals have propagated through their respective reference and measurement arms, the signals are combined, whereas in the Michelson interferometer, after the signals have propagated through their respective arms they are reflected back through the arms again where they are then combined. The combined beams produce an interference pattern with bright and dark regions indicative of the phase of the signal beam relative to the reference. The dependence of the brightness of the interference pattern on the relative phase and amplitude is complicated. The interferometers are sensitive to noise, and the algorithms involved in performing the phase retrieval and comparisons are cumbersome, involving lengthy calculations and introducing errors.

SUMMARY OF THE INVENTION

An optical quadrature interferometer according to the present invention includes a light source which may be polarized or an unpolarized light source and a polarizer, and a beamsplitter which splits the light provided by the light source into two signals which are in a defined phase relationship with each other. In one path a quarter wave plate is used to convert the polarization of the light to circular. This circularly polarized light can be represented by equal amounts of vertically and horizontally polarized light with a phase difference of 90° between them. The circularly polarized signal is then transmitted through a target and the resulting signal is combined with the reference signal. The combined signal is then directed through a polarizer which can switch between vertical polarization and horizontal polarization or alternatively through a polarizing beamsplitter. The combined signal can thus be separated into two separate fields which are in quadrature with each other. An image processing algorithm can then obtain the in-phase and quadrature information and provide detailed images of the amplitude and phase of the target.

BRIEF DESCRIPTION OF THE DRAWINGS

The invention will be more fully understood from the following detailed description taken in conjunction with the accompanying drawings in which.

DESCRIPTION OF THE PREFERRED EMBODIMENT

Figure 1:
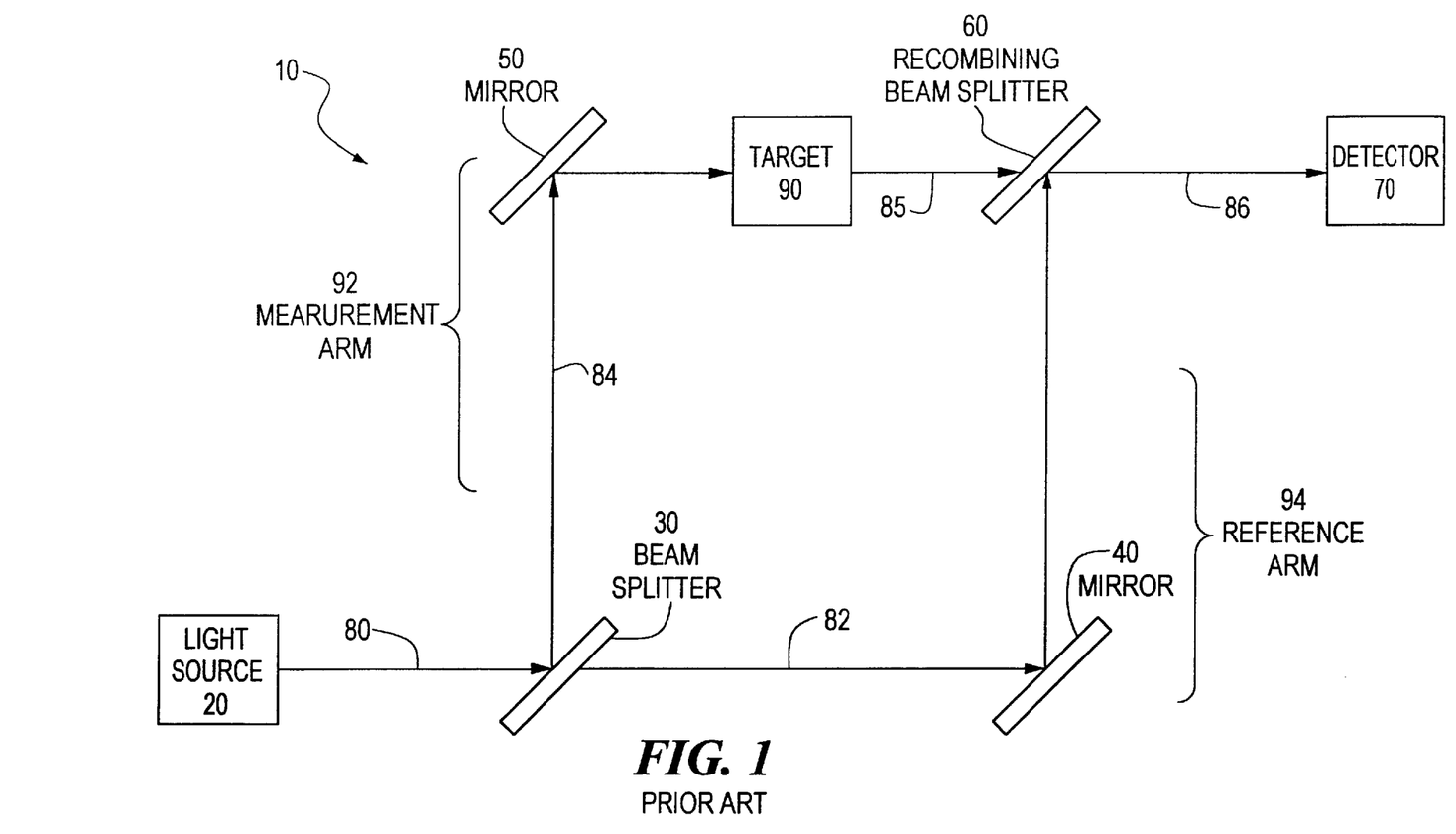
FIG. 1 is a diagram of a prior art Mach-Zender type interferometer.

FIG. 1 shows a prior art Mach-Zender interferometer 10. This interferometer comprises a light source 20, such as a laser, providing a beam of light 80 which is directed to a beamsplitter 30. The beamsplitter 30 splits the beam of light 80 into two secondary beams 82 and 84 which are in phase with each other. The beamsplitter 30 is angled with respect to light source 20 such that the reflected beam is directed along an axis which is different than that of light beam 80. Although angles of approximately ninety degrees are shown in the Figures, it should be appreciated that any angle could be used. The first secondary beam 82 is the portion that passes through the beamsplitter 30. This first secondary beam 82 is directed to a first mirror 40, which is angled to reflect the first secondary light beam 82 along a different axis to a recombining beamsplitter 60. This path, from beamsplitter 30 to first mirror 40 then to recombining beamsplitter 60 comprises the reference arm 94, and provides for a beam unaffected by the target 90.

Second secondary beam 84 is the light beam reflected by the beamsplitter 30 which is angled such that the reflected light is directed to a second mirror 50. Second mirror 50 is angled such that the second secondary beam 84 is directed through a target 90. The second secondary beam 84 is subjected to a phase change by passing through target 90 resulting in measurement beam 85. This path from beamsplitter 30, to mirror 50, through target 90, to recombining beamsplitter 60 comprises the measurement arm 92.

First secondary beam 82 and measurement beam 85 are combined by recombining beamsplitter 60 to provide resulting beam 86. Recombining beamsplitter 60 is angled such that resulting beam 86 is directed to detector 70. Any difference in phase between first secondary beam 82 and measurement beam 85 can be determined by analysis of resulting beam 86 by detector 70. A phase retrieval algorithm is used to determine the density and optical thickness or other characteristics of the target 90.

Figure 2:
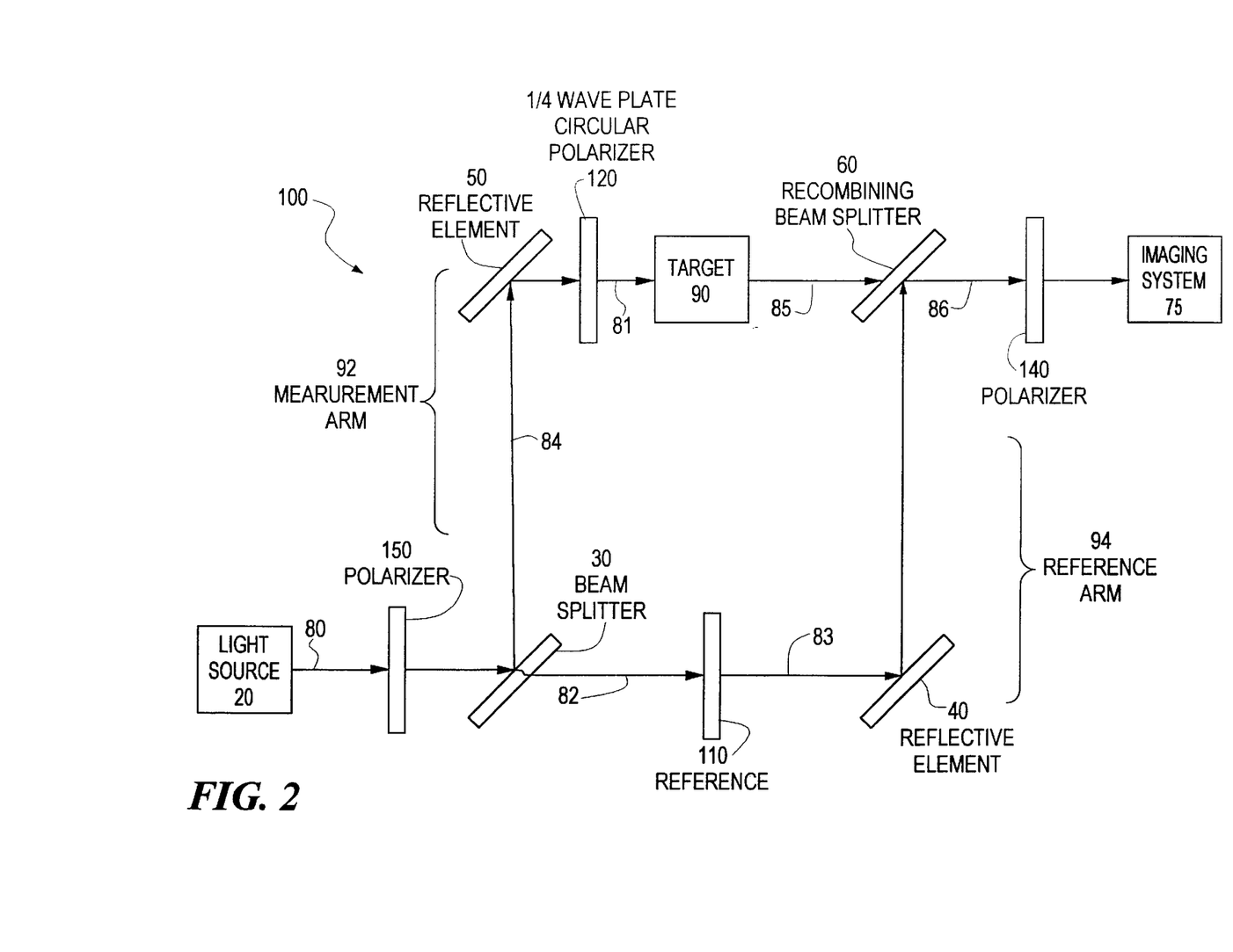
FIG. 2 is a diagram of a first implementation of an optical quadrature interferometer.

Referring now to FIG. 2 a first implementation of an optical quadrature interferometer 100 is shown. The optical quadrature interferometer 100 is based on a Mach-Zender interferometer and comprises a light source 20, such as a laser, providing a beam of light 80 which is directed to a beamsplitter 30. When a light source 20 which is not well polarized is used, a polarizer 150 which polarizes the light at 45° to the vertical, may be inserted between the light source 20 and the beamsplitter 30. Other angles are also possible, provided that a corresponding change is made at the output. If a well polarized light source is used, polarizer 150 is not necessary. The beamsplitter 30 splits the beam of light 80 into two secondary beams 82 and 84 which are in phase with each other. The beamsplitter 30 is angled such that a portion of the beam 84 is reflected along a different axis than that of beam 80, and a portion of the beam 82 passes through the beamsplitter 30.

The portion of light reflected by beamsplitter 30 is the second secondary light beam 84. This beam is directed through a quarter wave plate 120 by second reflective element 50. The quarter wave plate 120 provides for a relative phase shift of Δ□=π/2 radians which is equivalent to a phase shift of 90° between horizontal and vertical components of phase shifted beam 81. Phase shifted beam 81 is then directed through target 90. As phase shifted beam 81 passes through target 90, phase shifted beam 81 may undergo a change in phase, amplitude or both, resulting in measurement beam 85. This path comprises the measurement arm 92.

The first secondary beam 82 is directed to a reference 110 which alters the phase of light beam 83 to nearly match that of beam 84. For example, if the target being measured was a test-tube of water containing a fiber to be measured, the compensation element would be a test-tube of water without the fiber, such that any phase or amplitude change resulting from the test-tube and water in the measurement arm is compensated for in the reference arm. Accordingly, the interference pattern will not contain high spatial-frequency components which would require very good spatial resolution. Compensated light beam 83 is directed to first reflective element 40. First reflective element 40 is angled to reflect the compensated beam 83 to an recombining beamsplitter 60. This path, from beamsplitter 30 through reference element 110, to first reflective element 40 and to recombining beamsplitter 60 comprises the reference arm 94.

Compensated light beam 83 and measurement beam 85 are combined by recombining beamsplitter 60 to provide resulting beam 86. Recombining beamsplitter 60 is angled such that resulting beam 86 is directed along a different axis than compensated light beam 83. Resulting beam 86 is directed through polarizer 140. Polarizer 140 is rotated between two positions, a first position where polarizer 140 is a horizontal polarizer, and a second position where polarizer 140 is a vertical polarizer. Polarizer 140 is used to separate the mixed polarization field of resulting beam 86 into two separate fields which are in quadrature with each other by rotating polarizer 140 between it's two positions. The beam resulting from polarizer 140 is directed to imaging system 75 which utilizes an image processing algorithm to obtain the in-phase and quadrature components of the signal, thereby providing interpretation of the data using both the magnitude and phase information.

The imaging system 75 may comprise a scattering screen such as ground glass or milk glass which is followed by a charge coupled device (CCD) camera or other television camera, and a computer system including a device for storing and retrieving image frames from the CCD camera. The imaging system may also comprise photographic film and an optical reconstruction system for producing holographic images from the processed film, or direct display on a CCD.

Figure 2A:
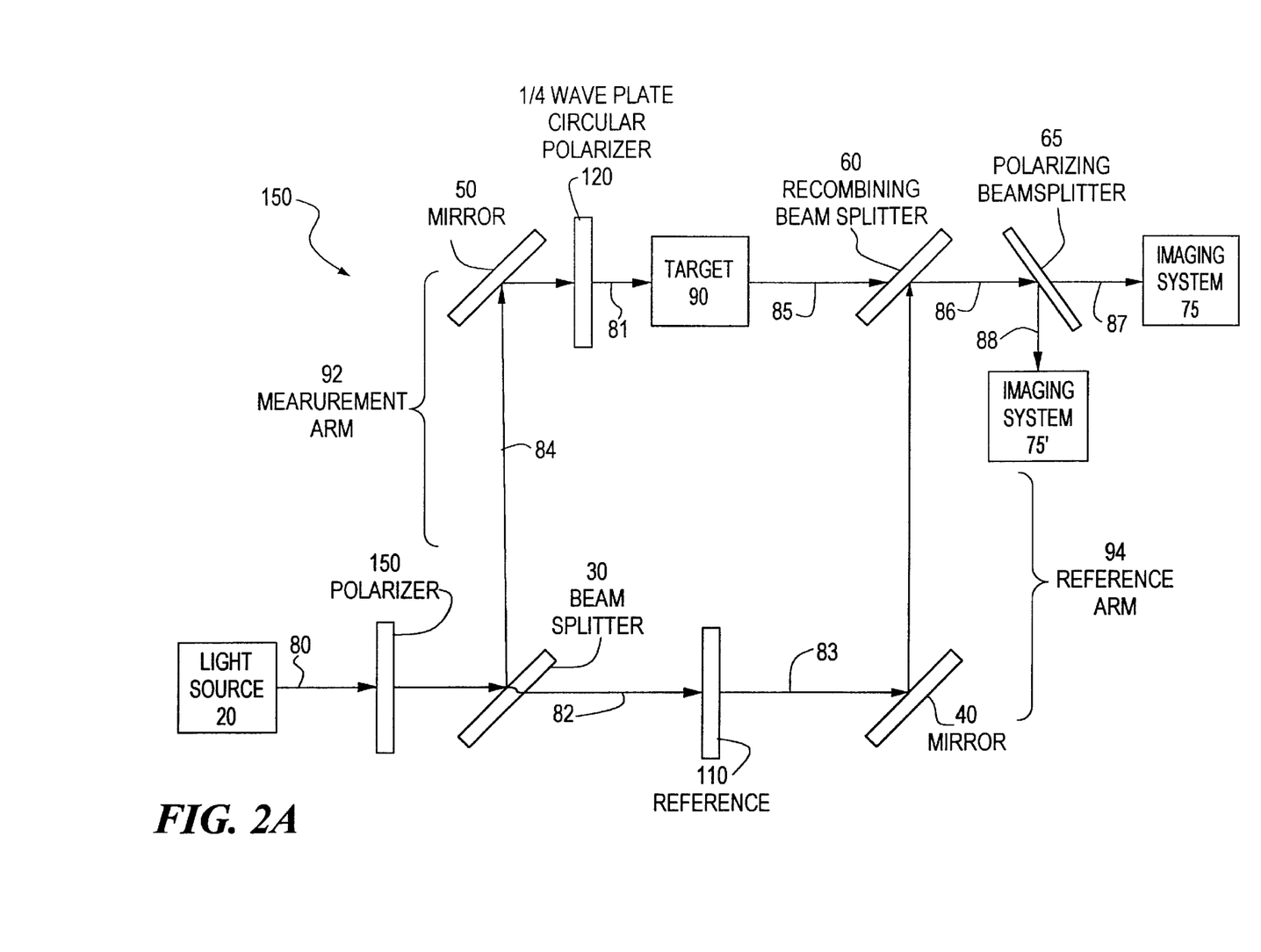
FIG. 2A is a diagram of the optical quadrature interferometer of FIG. 2 including an additional imaging system.

Referring now to FIG. 2A, an optical quadrature interferometer 150 is shown. This optical quadrature interferometer is similar to the one shown in FIG. 2 except that recombining beamsplitter 60 has been replaced with polarizing beamsplitter 65, polarizer 140 has been removed, and a dual channel imaging system 75 and 75' are implemented to provide interpretation of the data using both the phase and magnitude information. Resultant beam 86 is directed to polarizing beamsplitter 65 which provides for two polarized output beams 87 and 88. Each polarized output beam 87 and 88 is provided to a respective imaging system 75 and 75'.

Figure 2B:
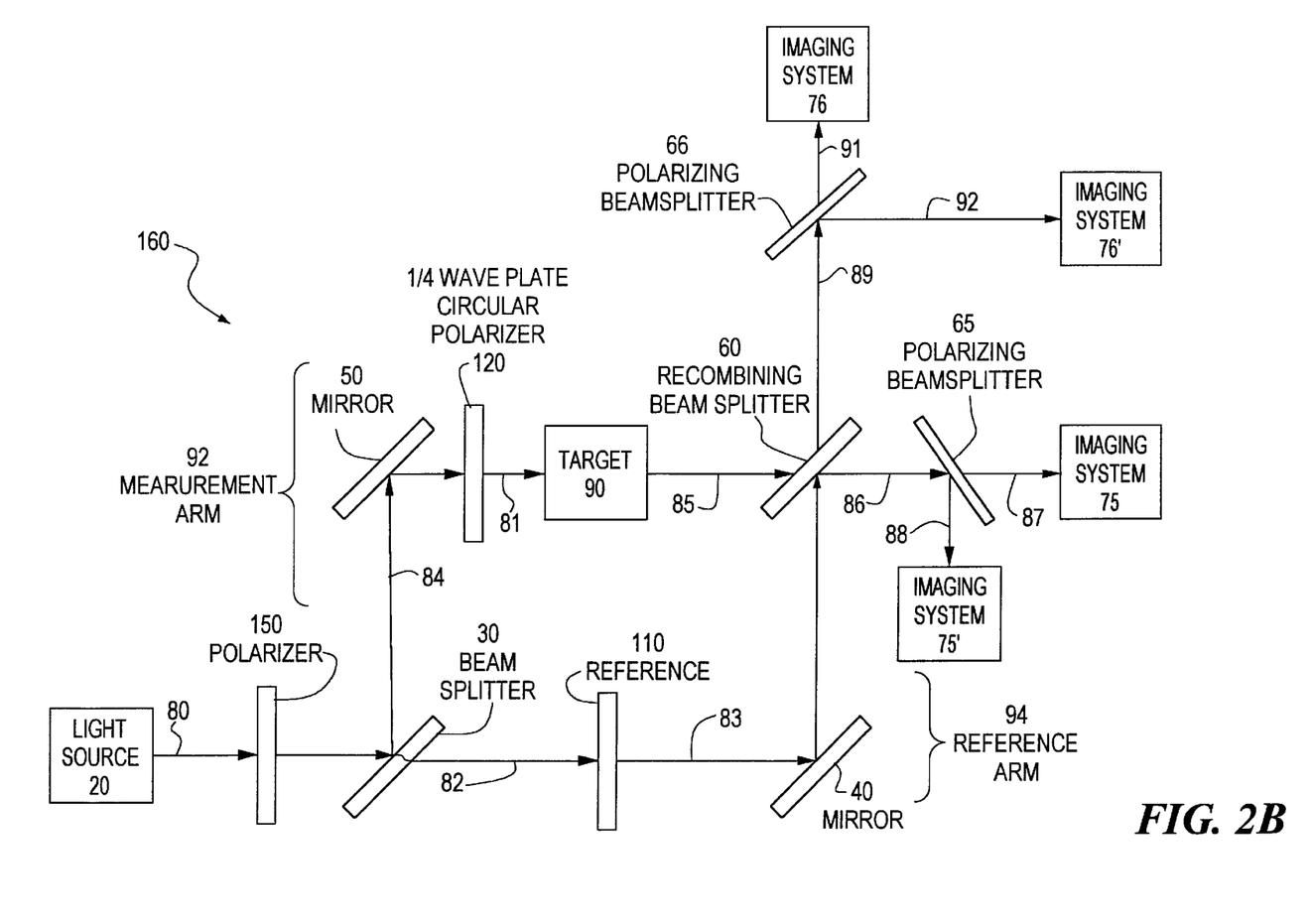
FIG. 2B is a diagram of the optical quadrature interferometer of FIG. 2A including an additional imaging system channel.

Referring now to FIG. 2B, an optical quadrature interferometer 160 is shown. This optical quadrature interferometer is similar to the one shown in FIG. 2A and includes an additional polarizing beamsplitter 66, and an additional dual channel imaging system 76 and 76'. A second resultant beam 89 is also provided by recombining beamsplitter 60. While this second resultant beam 89 is ignored in other embodiments, it is utilized in this embodiment. Second resultant beam 89 is directed to second polarizing beamsplitter 66 which provides for two polarized output beams 91 and 92. Each polarized output beam 91 and 92 are provided to a respective imaging system 76 and 76', thus providing for a four channel imaging system.

Figure 3:
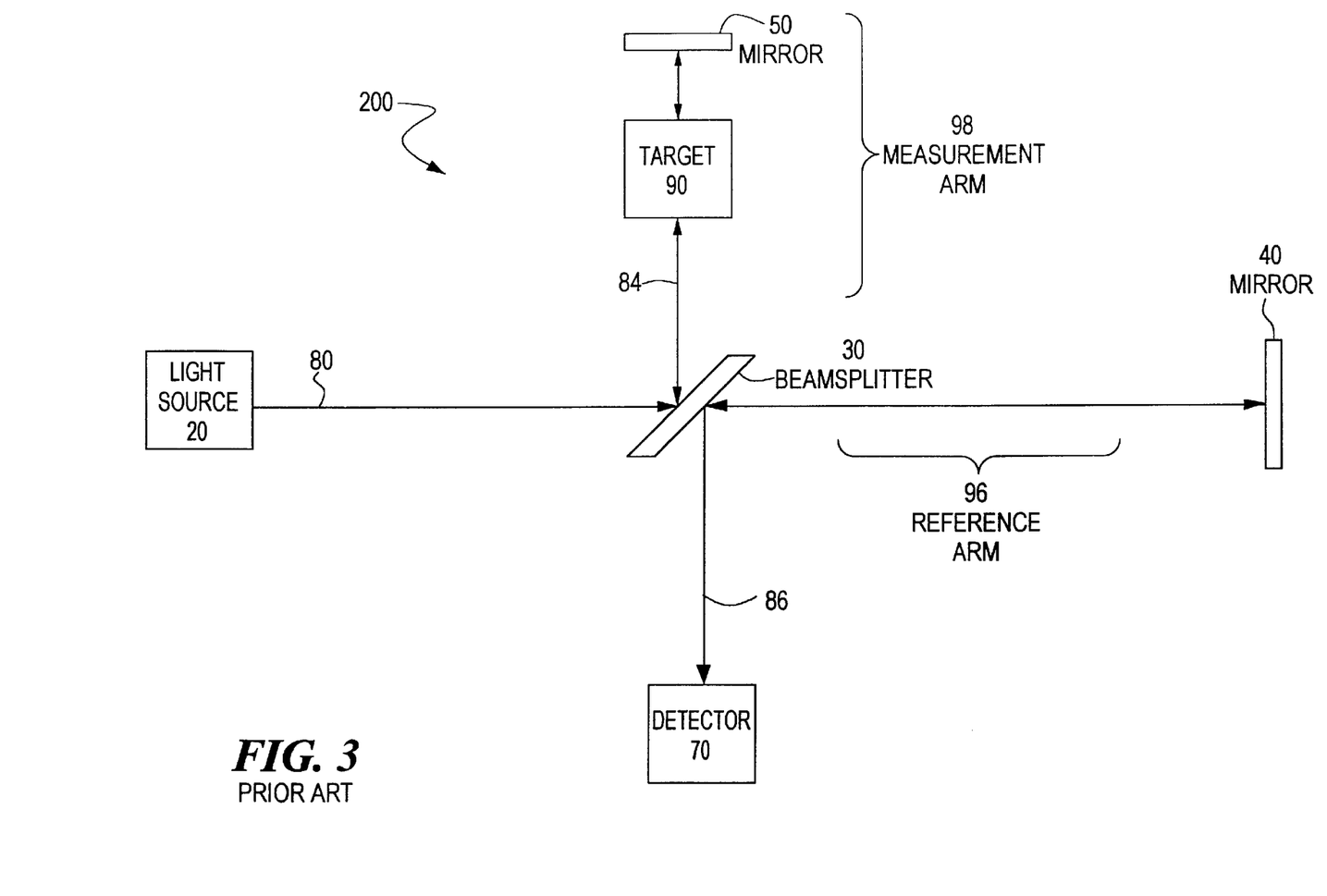
FIG. 3 is a diagram of a prior art Michelson type interferometer.

Referring now to FIG. 3, a prior art Michelson interferometer 200 is shown. A light source 20, such as a laser, provides a beam of light 80 which is directed to a beamsplitter 30. The beamsplitter 30 splits the beam of light 80 into two secondary beams 82 and 84 which are in phase with each other. The first secondary beam 82 is the portion that passes through the beamsplitter 30. This light beam is directed to a first mirror 40, which is angled to deflect the first secondary light beam along the same axis back to the beamsplitter 30. This path is the reference arm 96, and provides for a beam unaffected by a target.

Second secondary beam 84 is the light beam reflected by the beamsplitter 30. Beamsplitter 30 is angled such that the reflected light is directed to a target 90 where secondary beam 84 undergoes a phase shift upon passing through target 90. The beam exiting target 90 is directed to second mirror 50. Second mirror 50 is angled so that the second secondary beam is directed back through the target 90. The second secondary beam is subjected to a second phase change by target 90. First secondary beam 82 and second secondary beam 84 are combined by beamsplitter 30 to provide resulting beam 86. Any difference in phase between first secondary beam 82 and second secondary beam 84 can be determined by analysis of resultant beam 86 by detector 70. A phase retrieval algorithm is used to determine the density, clarity or other characteristics of the target 90.

Figure 4:
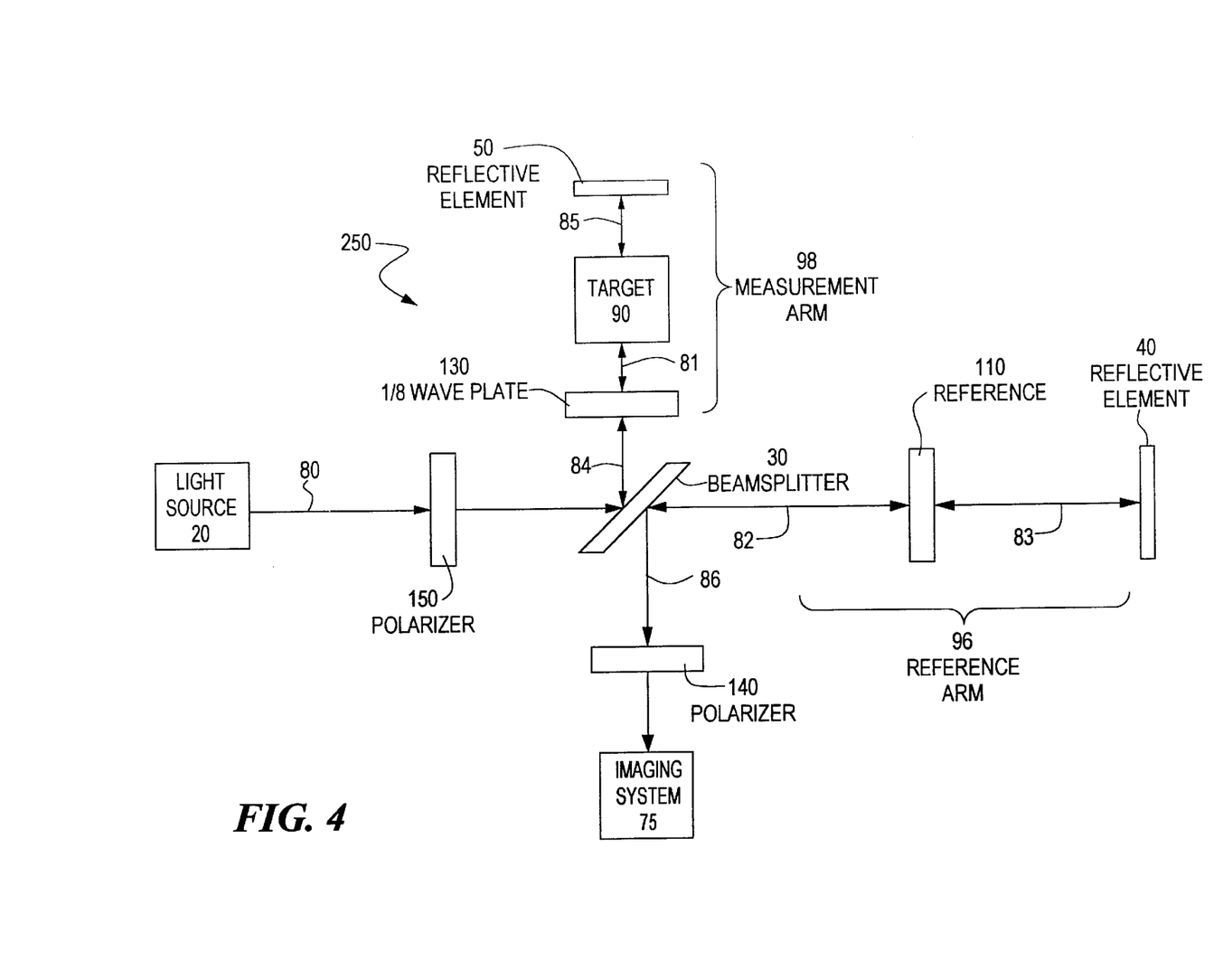
FIG. 4. is a diagram of an additional implementation of an optical quadrature interferometer.

FIG. 4 shows an embodiment of an optical quadrature interferometer 250 based on a Michelson interferometer. The optical quadrature interferometer 250 comprises a light source 20, such as a laser, providing a beam of light 80 which is directed to a beamsplitter 30. An optional polarizer 150 which polarizes the light at 45° (or other suitable angle) to the vertical may be used if the light source 20 is not well polarized. The beamsplitter 30 splits the beam of light 80 into two secondary beams 82 and 84 which are in a known phase relationship with each other. The first secondary beam 82 is directed to a reference 110 resulting in compensated light beam 83. Compensated light beam 83 is then directed to a first reflective element 40. First reflective element 40 is oriented such that the compensated light beam is reflected back along the same axis, through reference 110, and to beamsplitter 30.

In the measurement arm 98 of the optical quadrature interferometer 250, the second secondary light beam 84 is directed through a one-eighth wave plate 130. The one-eighth wave plate 130 provides for a relative phase shift of Δø=π/4 radians which is equivalent to a phase shift of 45° between the vertical and horizontal components of the beam entering the one-eighth wave plate 130. Beam 81 is then directed through target 90, where it undergoes a change in phase, amplitude or both; resulting in measurement beam 85. Measurement beam 85 is then directed to second reflective element 50 which is oriented so that beam 85 is reflected back through target 90, then through one-eighth wave plate 130, where the beam is phase shifted another 45°, resulting in the beam being shifted a total of 90° between the vertical and horizontal polarization components of the beam, not including any phase shift as a result of the beam passing through the target 90.

Compensated light beam 83 and measurement beam 85 are combined by beamsplitter 30 to provide resulting beam 86. Resulting beam 86 is then directed to polarizer 140 which is used to separate the mixed polarization field into two separate fields which are in quadrature with each other by rotating polarizer 140. Polarizer 140 is rotated between two positions, a first position where polarizer 140 is a horizontal polarizer, and a second position where polarizer 140 is a vertical polarizer. Polarizer 140 is used to separate the mixed polarization field of resulting beam 86 into two separate fields which are in quadrature with each other by rotating polarizer 140 between it's two positions. The beam resulting from polarizer 140 is directed to imaging system 75 which uses an image processing algorithm to obtain the in-phase and quadrature components of the signal, thereby providing interpretation of the data using both the magnitude and phase information.

Figure 4A:
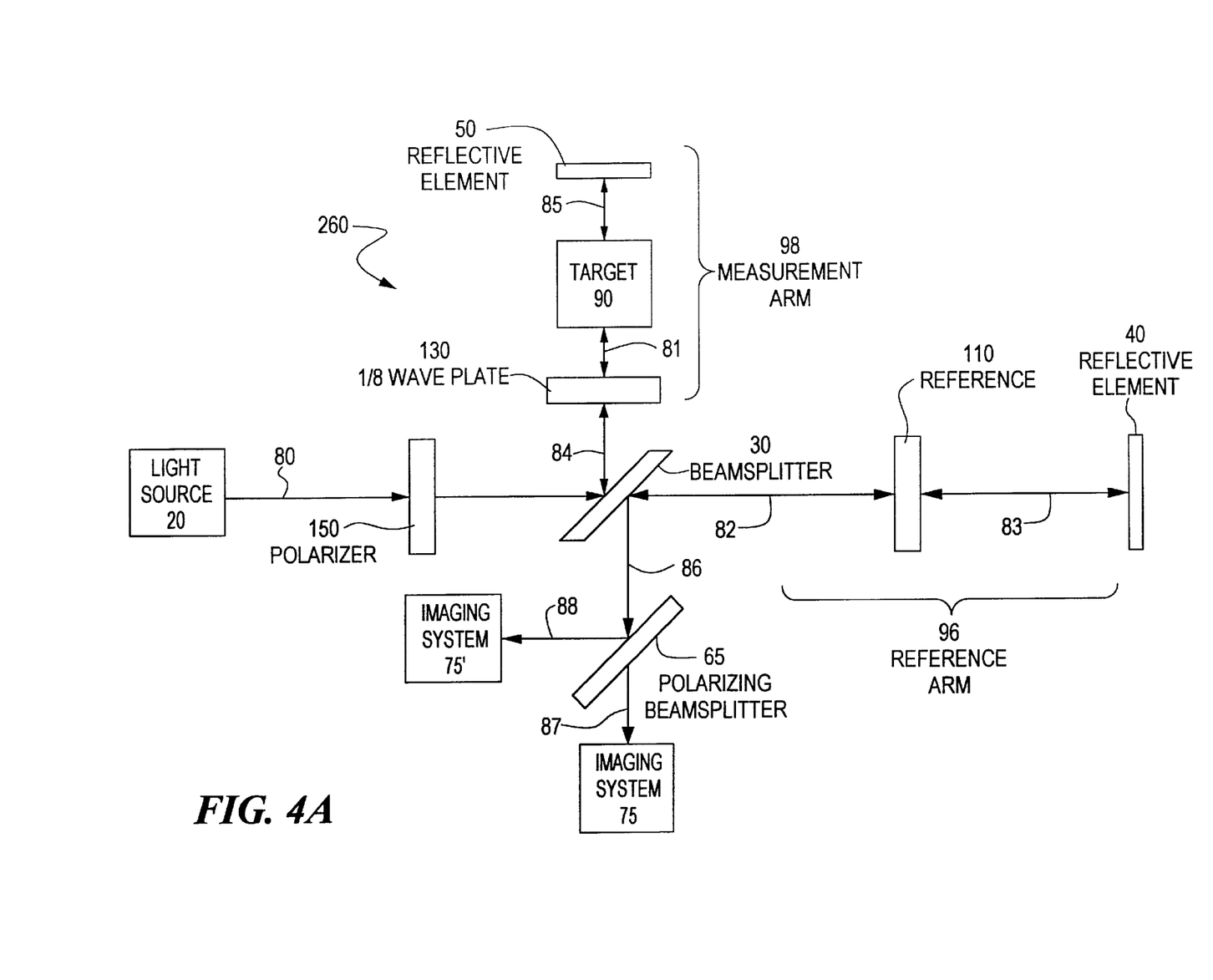
FIG. 4A is a diagram of the optical quadrature interferometer of FIG. 4 including an additional imaging system.

Referring now to FIG. 4A, an optical quadrature interferometer 260 is shown. This optical quadrature interferometer is similar to the one shown in FIG. 4 except that polarizer 140 has been replaced with polarizing beamsplitter 65, and a dual channel imaging system 75 and 75' is implemented to provide interpretation of the data using both the phase and magnitude information. Resultant beam 86 is directed to polarizing beamsplitter 65 which provides for two polarized output beams 87 and 88. Each polarized output beam 87 and 88 is provided to a respective imaging system 75 and 75'.

Additional embodiments may include the use of any type of laser as the light source 20; a light source 20 having a short coherence length, such as a light emitting diode (LED); a superluminescent diode; a dye laser; a gas-discharge lamp; a tungsten filament lamp; a mercury arc lamp or similar type light source. A collimator or focussing system may be installed within the interferometer to change the intensity of the light beam. The imaging system 75 may include any type of imaging system, including photographic film and an optical reconstruction system to produce a holographic image of the medium being measured. In an alternate embodiment the image may be recovered by an imaging system utilizing diffraction tomography. Power reducing filters may be implemented in either arm of the interferometer when using cameras of limited irradiance resolution, such as 8-bit CCD cameras, as part of the imaging system.

By use of polarization in the optical quadrature interferometer to obtain the in-phase and quadrature information, the interferometry is more accurate and does not require phase retrieval algorithms. Additionally, the optical quadrature interferometer can be utilized in performing optical coherence tomography faster and at less expense, and holograms can be produced without ghost images. The optical quadrature interferometer may be used in applications such as non-destructive testing of optical fibers; transillumination imaging through turbid media, medical imaging through tissue such as performing mammography at optical wavelengths; and for vibration analysis.

Having described preferred embodiments of the invention it will now become apparent to those of ordinary skill in the art that other embodiments incorporating these concepts may be used. Accordingly, it is submitted that the invention should not be limited to the described embodiments but rather should be limited only by the spirit and scope of the appended claims.

We claim:
1. An optical quadrature interferometer comprising:
   a light source providing a beam of light;
   a beamsplitter oriented at an angle with respect to said light source, said beamsplitter receiving said beam of light and splitting said beam of light into a first secondary light beam and a second secondary light beam, said first secondary light beam and said second secondary light beam having approximately the same frequency as said beam of light;
   a recombining beamsplitter;
   a first reflective element oriented such that said first reflective element receives said first secondary light beam and reflects said first secondary light beam along a different axis to said recombining beamsplitter;
   a second reflective element receiving said secondary light beam and oriented to direct said secondary light beam along a different axis;
   a quarter wave plate receiving said second secondary light beam from said second reflective element, said quarter wave plate providing a 90° phase shift between vertically and horizontally polarized components of the beam resulting in a circularly polarized light beam;
   a target receiving said circularly polarized light beam, said target causing a change to said circularly polarized light beam as said circularly polarized light beam passes through said target resulting in a measurement light beam;
   said recombining beamsplitter combining said measurement light beam with said first secondary light beam to provide a resultant light beam;
   a polarizing element receiving the resultant light beam and separating said resultant light beam into two separate fields which are in quadrature with each other; and
   an imaging system for displaying data provided by said polarizing element.

2. The optical quadrature interferometer of claim 1 wherein said polarizing element comprises at least one polarizer in communication with at least one said imaging system.

3. The optical quadrature interferometer of claim 1 wherein said polarizing element comprises at least one polarizing beamsplitter in communication with at least one said imaging system.

4. The optical quadrature interferometer of claim 1 wherein said polarizing element comprises at least one polarizer in communication with at least one said imaging system and at least one polarizing beamsplitter in communication with at least one said imaging system.

5. The optical quadrature interferometer of claim 1 wherein the change to said circularly polarized light beam by said target comprises a phase shift.

6. The optical quadrature interferometer of claim 1 wherein the change to said circularly polarized light beam by said target comprises a change in amplitude.

7. The optical quadrature interferometer of claim 1 further comprising a second polarizer disposed between said light source and said beamsplitter.

8. The optical quadrature interferometer of claim 1 further comprising a reference element disposed between said beamsplitter and said recombining beamsplitter.

9. The optical quadrature interferometer of claim 1 wherein said imaging system comprises a scattering screen followed by a charge coupled device camera and a computer.

10. The optical quadrature interferometer of claim 1 wherein said imaging system comprises photographic film and an optical reconstruction system.

11. The optical quadrature interferometer of claim 1 wherein said imaging system utilizes diffraction tomography.

12. The optical quadrature interferometer of claim 1 wherein said light source comprises a laser.

13. The optical quadrature interferometer of claim 1 wherein said light source comprises a light source having a short coherence length.

14. The optical quadrature interferometer of claim 13 wherein said light source having a short coherence length is chosen from a group comprising a light emitting diode, a superluminescent diode, a dye laser, a gas discharge lamp, a tungsten filament lamp, and a mercury arc lamp.

15. An optical quadrature interferometer comprising:

a light source providing a beam of light;

a beamsplitter oriented at an angle with respect to said light source, said beamsplitter receiving said beam of light and splitting said beam of light into a first secondary light beam and a second secondary light beam, said first secondary light beam and said second secondary light beam having approximately the same frequency as said beam of light;

a first reflective element oriented such that said first reflective element receives said first secondary light beam and reflects said first secondary light beam along a same axis to said beamsplitter;

a second reflective element;

a one-eighth wave plate disposed between said second reflective element and said beamsplitter, said one-eighth wave plate providing a 45° phase shift between vertically and horizontally polarized components of the second secondary light beam;

a target disposed between said second reflective element and said beamsplitter, said target causing a change in said secondary light beam as said secondary light beam passes through said target;

said second reflective element receiving said secondary light beam after said secondary light beam has traversed through said one-eighth wave plate and said target, said second reflective element oriented to direct said secondary light beam along a same axis back through said target and said one-eighth wave plate;

said beamsplitter combining said first secondary light beam with said second secondary light beam after said secondary light beam has traversed the path from said beamsplitter through said one-eighth wave plate, through said target to said second reflective element and back through said target and said one-eighth wave plate to provide a resultant light beam;

a polarizing element receiving the resultant light beam and separating said resultant light beam into two separate fields which are in quadrature with each other; and an imaging system for displaying data provided by said polarizing element.

16. The optical quadrature interferometer of claim 15 wherein said polarizing element comprises a polarizer, said polarizer in communication with said imaging system.

17. The optical quadrature interferometer of claim 15 wherein said polarizing element comprises a polarizing beamsplitter, said polarizing beamsplitter in communication with at least one said imaging system.

18. The optical quadrature interferometer of claim 15 wherein said change to said phase shifted light beam by said target comprises a phase shift.

19. The optical quadrature interferometer of claim 15 wherein said change to said phase shifted light beam by said target comprises a change in amplitude.

20. The optical quadrature interferometer of claim 15 further comprising a second polarizer disposed between said light source and said beamsplitter.

21. The optical quadrature interferometer of claim 15 further comprising a reference element disposed between said beamsplitter said first reflective element.

22. The optical quadrature interferometer of claim 15 wherein said imaging system comprises a scattering screen followed by a charge coupled device camera and a computer.

23. The optical quadrature interferometer of claim 15 wherein said imaging system comprises photographic film and an optical reconstruction system.

24. The optical quadrature interferometer of claim 15 wherein said imaging system utilizes diffraction tomography.

25. The optical quadrature interferometer of claim 15 wherein said light source comprises a laser.

26. The optical quadrature interferometer of claim 15 wherein said light source comprises a light source having a short coherence length.

27. The optical quadrature interferometer of claim 26 wherein said light source having a short coherence length is chosen from a group comprising a light emitting diode, a superluminescent diode, a dye laser, a gas discharge lamp, a tungsten filament lamp and a mercury arc lamp.

* * * * *

UNITED STATES PATENT AND TRADEMARK OFFICE
CERTIFICATE OF CORRECTION

PATENT NO    : 5,883,717
DATED        : March 16, 1999
INVENTOR(S)  : Charles A. DiMarzio et al.

It is certified that error appears in the above-identified patent and that said Letters Patent is hereby corrected as shown below:

Title page, item [57],
Abstract, line 9, "the to reference arm" should read --the reference arm--

Column 3, line 3, "$\Delta[] = \pi/2$ should read --$\Delta\Phi = \pi/2$--

Signed and Sealed this

Twenty-seventh Day of February, 2001

Attest:

NICHOLAS P. GODICI

Attesting Officer    Acting Director of the United States Patent and Trademark Office